United States Patent
Kalies (10) Patent No.: US 7,657,437 B2
(45) Date of Patent: Feb. 2, 2010

(54) METHOD FOR CONDUCTING PRESCRIPTION DRUG CO-PAYMENT PLANS

(75) Inventor: Ralph F. Kalies, Pickett, WI (US)

(73) Assignee: Omnicare, Inc., Covington, KY (US)

( * ) Notice: Subject to any disclaimer, the term of this patent is extended or adjusted under 35 U.S.C. 154(b) by 831 days.

(21) Appl. No.: 10/608,265

(22) Filed: Jun. 27, 2003
(Under 37 CFR 1.47)

(65) Prior Publication Data
US 2004/0073457 A1   Apr. 15, 2004

Related U.S. Application Data

(60) Provisional application No. 60/392,066, filed on Jun. 27, 2002.

(51) Int. Cl.
| | |
|---|---|
| G06Q 10/00 | (2006.01) |
| G06Q 30/00 | (2006.01) |
| G06Q 50/00 | (2006.01) |
| G06Q 40/00 | (2006.01) |
| A61B 5/00 | (2006.01) |
| G06F 19/00 | (2006.01) |

(52) U.S. Cl. .................. 705/1; 705/2; 705/3; 705/4
(58) Field of Classification Search ............ 705/2–3
See application file for complete search history.

(56) References Cited

U.S. PATENT DOCUMENTS

| | | | | |
|---|---|---|---|---|
| 4,858,121 | A | 8/1989 | Barber et al. | 364/406 |
| 5,301,105 | A | 4/1994 | Cummings, Jr. | 364/401 |
| 5,704,044 | A | 12/1997 | Tarter et al. | 395/204 |
| 5,845,255 | A * | 12/1998 | Mayaud | 705/3 |
| 6,012,035 | A * | 1/2000 | Freeman et al. | 705/2 |
| 6,208,973 | B1 | 3/2001 | Boyer et al. | 705/2 |
| 6,317,719 | B1 | 11/2001 | Schrier et al. | 705/2 |
| 6,341,265 | B1 | 1/2002 | Provost et al. | 705/4 |
| 6,343,271 | B1 | 1/2002 | Peterson et al. | |
| 2001/0037216 | A1 * | 11/2001 | Oscar et al. | 705/2 |
| 2002/0002495 | A1 * | 1/2002 | Ullman | 705/21 |
| 2002/0111832 | A1 * | 8/2002 | Judge | 705/3 |

* cited by examiner

*Primary Examiner*—C. Luke Gilligan
*Assistant Examiner*—Sheetal R Rangrej
(74) *Attorney, Agent, or Firm*—Ostrolenk Faber LLP (57) ABSTRACT

A credit card-based prescription benefits plan utilizes an electronic means for telecommunication to rapidly adjudicate prescription claims. The adjudication process includes a third-party claims processor interposed the pharmacy and the patient's credit card clearinghouse to ensure that the subscriber receives all benefits available under the plan. The third-party claims processor may also provide patient counseling and advocacy by performing patient-specific drug regimen reviews to check for potential adverse drug reactions and drug interactions.

13 Claims, 3 Drawing Sheets

METHOD FOR CONDUCTING PRESCRIPTION DRUG CO-PAYMENT PLANS

This application claims the benefit of U.S. Provisional Patent Application No. 60/392,066, filed Jun. 27, 2002.

FIELD OF THE INVENTION

This invention relates to a method for carrying out prescription drug co-payment plans. Specifically, the invention relates to a method for ensuring the proper discounting of prescriptions purchased under prescription co-payment plans and for ensuring patient advocacy.

BACKGROUND OF THE INVENTION

Spending on prescription drugs continues to be one of the fastest-growing healthcare costs facing consumers. Factors that have driven the increases in drug spending include increased use of disease-preventative and quality-of-life enhancing drugs by patients, direct marketing to patients by pharmaceutical companies, changes in use to newer, higher-cost drugs, and price increases by manufacturers. A particular problem with prescription drug costs is that many patients who lack prescription drug coverage often pay more for prescriptions than those who do have coverage. This is usually due to "cost shifting" by pharmacies, who attempt to collect larger profit margins from patients with limited buying power to compensate for the reduced profits available from insured patients having prescription plans with negotiated price schedules. The result is that uninsured patients, who have little or no market leverage as individuals, pay higher prices for prescriptions than other payers in the marketplace, such as third party payers, insurance companies, the government and the like. In order to assist those individuals who lack prescription drug coverage, discount drug card programs have been employed by Prescription Benefit Management ("PBM") companies and others wherein subscribers to the programs receive monetary discounts from participating pharmacies. Even though such plans are usually "100% co-pay," meaning that the patient pays 100% of the net price for the prescription drug at the time of dispensing, the plans are intended to provide price discounts to patients as a result of the PBM's buying power and contracts with participating pharmacies. Under such contracts the PBM negotiates a discounted price for prescriptions for its subscribers. Many discount prescription drug card plans also include some form of patient advocacy. A common form of patient advocacy is a drug regimen review ("DRR"), which is a process of reviewing the patient's medical history and current medications to check for potential drug-related problems relative to a prescribed medication alone or in concert with other prescriptions that the patient may be taking. A DRR may check for such potential problems as adverse reactions, drug/drug interactions, therapeutic duplication and overutilization. Another patient advocacy function is to ensure that the drugs prescribed for the patient are listed on an approved "formulary." In general, a formulary is a list of drugs that are considered by a prescription benefits plan to be the preferred treatment for a patient's condition among medical equivalents. The criteria for the preferences may be for medical reasons such as safety and efficacy. Other criteria may include economic considerations such as cost-containment and market-share shifting. However, since the discount drug card programs require that the patient pay 100% of the price of the prescription at the time they receive the medication, and since the pharmacist is not required to coordinate benefits or discounts through a third party, there is no assurance that the patient will receive the discounted price and patient advocacy that the pharmacy had contracted to provide under the terms of the discount drug card program. Pharmacies are generally not motivated to incur the additional expense and labor of a discount card program without a financial benefit or incentive to do so. Thus, under a non-monitored prescription drug discount card program wherein the pharmacy receives 100% of the payment directly from the patient at the time of dispensing there are few, if any, checks and balances to hold the pharmacist accountable to a third party for payment for their services. The result is that the patient may not derive the expected benefit from being a subscriber to a prescription drug discount program.

The Centers For Medicare and Medicaid Services ("CMS") have proposed a program that includes a CMS discount card that is essentially a 100% co-pay discount card that would be offered by approved PBMs throughout the country. The PBMs would be required to undergo an application process to be approved for participation in a CMS endorsed program. The patient could then use their card to have their prescriptions filled at participating pharmacies. A shortcoming of the CMS plan, like others in the art, is that there is a decreased likelihood that the patient will receive all of the intended benefits since there is no requirement or incentive for the pharmacy to follow the program procedures or coordinate with the PBM. Likewise, under the CMS plan there is no assurance that the participating pharmacies will offer patients a proper discount on their prescription prices since there no means of holding the pharmacies accountable for bypassing reporting procedures. Under the CMS program there is a suggested opportunity to share a portion of rebates received by the PBMs with the patients. However there is nothing in the CMS program mandating that the PBM share in any of those savings. Overall, the CMS plan is not expected to be very effective.

There is an abundance of 100% co-pay drug discount programs. For example, nearly every major PBM offers such a program. In addition, many major chain pharmacies have designed their own 100% co-pay programs. Discount plans have also been offered by pharmaceutical companies for their particular brands of drug products. Still other 100% co-pay programs are sponsored by large membership groups such as AARP. Some discount programs are business enterprises, such as a nationally-advertised discount prescription card program known as The Peoples' Prescription Card ("PPC"). For a monthly subscription fee, PPC advertises that subscribers will receive a range of discounts for prescriptions filled at either participating pharmacies throughout the country or through a mail-order prescription service. Although these plans have various benefits and features, they all suffer from a common shortcoming in that the patient is not assured of receiving the proper discount and patient advocacy.

Since the current 100% co-pay programs are generally ineffective, many patients are unable to purchase needed medication because it is too expensive. Such patients are considered to be "undertreated." Undertreated patients are prone to chronic disease and multiple chronic diseases, and often must be hospitalized at a greater expense to the healthcare system. Further, many hospital admissions of seniors are a result of drug related problems such as adverse reactions and drug interactions. There is a need for a prescription drug benefit program that consistently provides drug price discounts and patient advocacy services while holding down the cost of the program.

SUMMARY OF THE INVENTION

The shortcomings of current prescription plans are overcome by providing an incentive to the pharmacy without increasing the net cost of the prescriptions to the patient. According to an embodiment of the present invention, a 100% co-pay program requires adjudication of each prescription wherein all payment, less a predetermined co-payment tendered by the patient, is issued to the participating pharmacy by a PBM.

To properly adjudicate the prescription, the PBM maintains an eligibility file for each subscriber containing, in part, the subscriber's current credit card information such as the card number, the type of credit card, and the expiration date of the credit card. The eligibility file may also contain the patient's demographic information, medical history, and a list of current medications. This information may be used by the PBM to adjudicate the prescription claim through the pharmacy when the prescription is presented. The adjudication process may include approval, price discounting and patient advocacy components. Patient advocacy may include a drug regimen review to ensure that the patient's physician has prescribed the proper product for them. The appropriateness of products may be based on economic factors such as whether equivalent products are available at a lower cost, or medical criteria such as potential adverse drug reactions and drug interactions.

Once the claim is approved by the PBM, the proper discounted price is determined and any patient advocacy issues are resolved. The PBM then directs the pharmacy to fill the prescription with instructions as to what portion of the prescription price it is to collect from the subscriber, typically a co-payment of $5-$10. The remaining portion of the prescription charges are billed to the credit card account listed in the subscriber's eligibility file. Thus, while the plan according to the present invention still requires a 100% co-pay by the uninsured subscriber, a significant portion of the pharmacy's compensation is provided through the PBM, providing an incentive for the pharmacy to adjudicate the subscriber's prescription claims with the PBM and assuring the subscriber of their discount and receipt of patient advocacy.

In an alternate embodiment of the present invention, there may be a tiered co-payment wherein certain prescriptions require a greater or lesser co-payment amount. The higher co-payment amount serves as an indicator to the patient that there is an opportunity for the subscriber's drug regimen to be enhanced by either decreasing the cost of the prescription by substituting a generic or other therapeutically equivalent product, or by switching to a product other than that prescribed by the physician for such reasons as lower cost, fewer side effects, and potential drug interactions. The higher co-pay amount encourages subscribers to ask their doctor for a lower cost alternative or a lower cost therapeutic equivalent, since they will be charged a higher net amount for the prescription at the time of purchase. This puts the subscriber directly into the prescription cost/product selection process and encourages them to seek out the most cost-effective medications. Conversely, a prescription identified as a low co-pay may be subject to fewer suggested substitutions or changes to the drug regimen. For example, if a $5 co-pay is charged for prescriptions categorized as "preferred" in a formulary, and a $10 co-pay is charged for prescriptions not listed as preferred, then the subscriber/patient would be charged the lower or higher co-payment at the time of the transaction, depending upon the formulary status of the medication. This provides feedback to the subscriber as to whether they are receiving the lowest cost and/or most appropriate medication. In a further example, for a preferred, or "on-formulary" prescription costing $100, the subscriber at the time of receiving the prescription would pay $5 to the pharmacy and the PBM would charge $95 to their credit card. If the prescription is off-formulary, the subscriber would pay $10 at the time of dispensing and then the PBM would charge $90 to their credit card. Thus, while the subscriber's final out-of-pocket cost is the same regardless of the prescribed medication's formulary status, the subscriber/patient becomes part of the drug selection process and has the ability to influence the dispensing of a more appropriate drug. A subscriber's involvement in the selection process is likely to increase after the first time a prescription is filled, since on subsequent visits to their doctor the patient is more likely to ask whether alternate medications having a lower co-payment (i.e., on-formulary) may be more appropriate.

The present invention benefits the overall healthcare system due to the reduced cost burden to plan sponsors. The patient subscriber also benefits through reduced healthcare cost. Further, taxpayers benefit because the present invention may lower the cost of CMS-related or other government-supported prescription benefit coverage. The present invention may also alleviate collateral healthcare costs for hospitalization and treatment of patients due to erroneous drugs being prescribed, drug interactions and inadequate patient treatment. These collateral costs can far outweigh the cost of the prescription drug program. Studies show that, for every dollar spent on prescription medications, four dollars are spent on treating drug-related problems. Eliminating even a portion of these drug-related problems through effective adjudication of prescription claims and patient advocacy can significantly reduce the cost of healthcare.

BRIEF DESCRIPTION OF THE DRAWINGS

Further features of the inventive embodiments will become apparent to those skilled in the art to which the embodiments relate from reading the specification and claims with reference to the accompanying drawings, in which:

DESCRIPTION OF THE PREFERRED EMBODIMENT(S)

Figure 1:
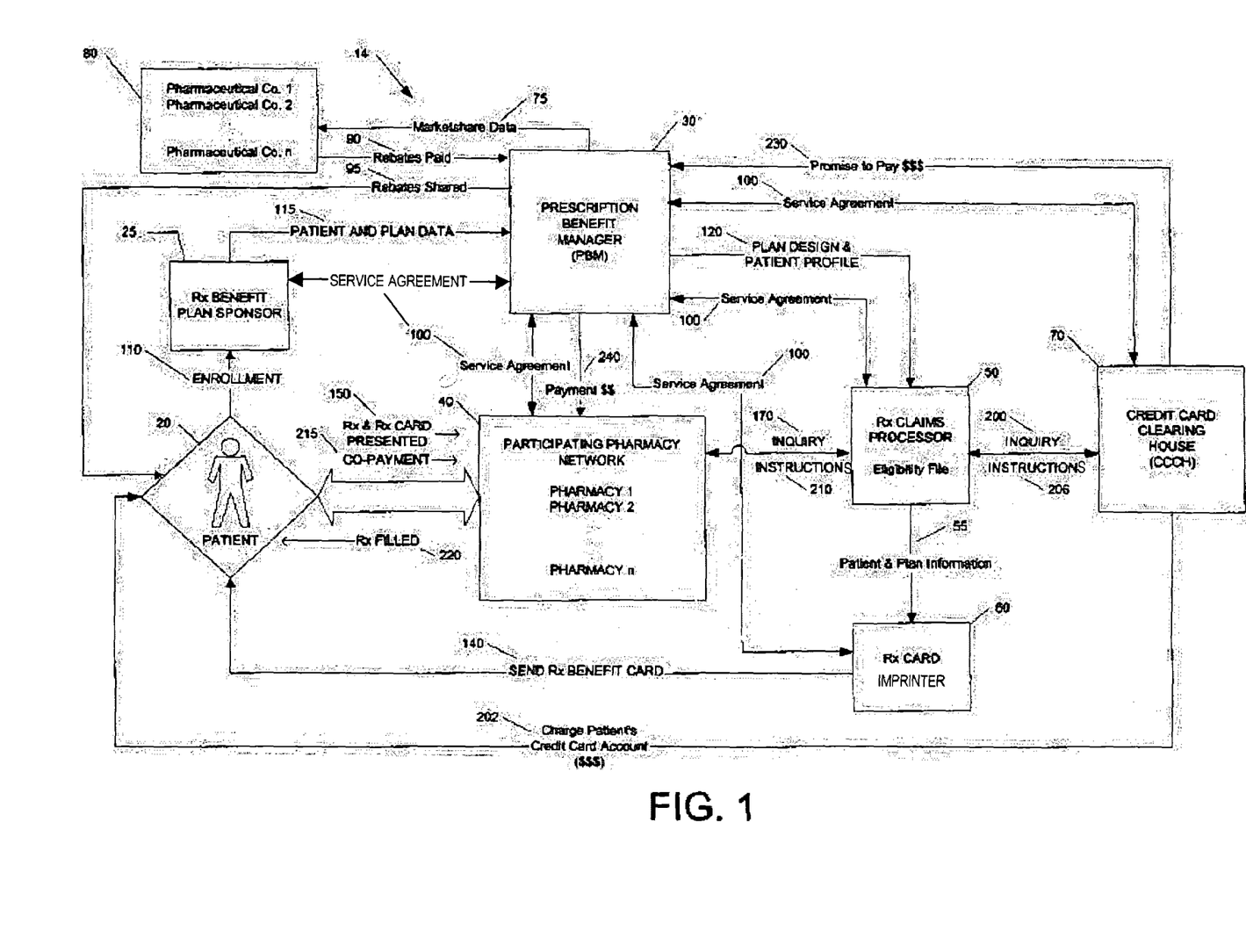
FIG. 1 is a block diagram of a discount prescription benefit card program in accordance with an embodiment of the present invention.

Referring first to FIG. 1, the primary parties involved in the prescription co-payment plan 14 (the "Plan") may include a patient/subscriber 20, a prescription benefits plan sponsor 25, a prescription benefits manager ("PBM") 30, a participating pharmacy network 40, a prescription claims processor 50, a prescription card imprinter 60, a credit card clearing house 70, and pharmaceutical companies, shown generally at 80. It should be noted that the terms "patient" and "subscriber" may be used interchangeably herein. A prescription benefits plan sponsor 25 first designs the Plan 14. The Plan 14 design essentially defines what medical products and prescription medications are covered, what portion of the cost the patient is responsible for, the amount of co-payment to be tendered by the patient at the time of dispensing, and what portion of the cost of the products and prescriptions the pharmacy is responsible for. The plan design also preferably includes a formulary of preferred medications.

To begin implementation of the Plan 14, the PBM 30 preferably enters into agreements, as at 100, with parties 25, 40, 50, 60 and 70, each of which become part of a service network and responsible for performance of a portion of the overall Plan. While there is no requirement that each of these parties be separately owned or operated, they are depicted in FIG. 1 as being independent entities for purposes of clarity. Communication between the parties 25, 40, 50, 60, 70 and any other involved parties is preferably accomplished via a means for electronic telecommunication. Example means for electronic telecommunication include computer networks, facsimile, the Internet, teletype, telephony, switches, high speed lines and frame relays.

Once the PBM 30 has established a service network for its Plan 14, the PBM solicits patients 20 to subscribe to the Plan 14, preferably through a prescription benefit plan sponsor 25. The plan sponsor 25 may be a membership-based group, such organizations, employers and governmental entities. When the patient 20 enrolls into the Plan 14, they provide the plan sponsor 25 with enrollment information. This information may include the subscriber's name, demographic data, age, gender, residence address, telephone number, social security number, election of benefit plan electives (such as co-payment amounts), and credit card account information. The enrollment process is represented generally at 110. Alternatively, the enrollment function of the plan sponsor 25 may be performed by the PBM 30.

The plan sponsor 25 combines the enrollment information from the patient/subscriber 20 with the Plan 14 design information. The sponsor then transmits the enrollment and Plan design information to the PBM 30 via the electronic means for communication, as shown generally at 115. The PBM 30 assembles a patient eligibility file by combining the enrollment and plan design information with other pertinent data, such as information about the plan sponsor 25 and any group or sub-group to which the patient 20 belongs. The patient eligibility file then undergoes account review and proofing, and is assigned identification information relating to the Plan 14 and the patient 20. The patient/subscriber 20 may be identified by a unique identification number, such as their social security number. However, other identification schemes may be implemented as long as they employ a method for unequivocally identifying a specific patient 20 and Plan 14 and do not permit ambiguity. The patient 20 generally will be assigned an account number, a group designation and a plan designation. Thus, each patient becomes associated with an account, as well as different groups or sub-groups within that account, such as executives, non-executives, or the like. Further defining the patient eligibility file are any other pertinent patient-specific benefit parameters. The patient eligibility files may be used with account activity records to decompile information for reporting purposes. For example, reports may be prepared for the plan sponsor 25 regarding the claim activity of a plurality of groups or divisions within that sponsor, according to the configuration of the Plan 14. Reports may also be generated showing the results of various data queries. Example queries include formulary compliance and high-usage drugs among the subscriber population, groups and sub-groups.

The assembled patient eligibility file is transmitted via the electronic means for telecommunications, as shown generally at 120, to the prescription claims processor 50. The prescription claims processor 50 stores the patient eligibility file for the purpose of adjudicating prescription benefit claims when they are presented to the pharmacy 40 by the patient 20, as shown at 150.

Once the eligibility file is provided to the claims processor 50, patient and plan information 55, typically comprising the patient's name, the plan sponsor, the group name, and specific plan designation are sent to a prescription card imprinter 60 which produces a prescription benefit identification card reflecting the patient 20 and Plan 14. The card imprinter 60 then forwards the prescription benefit identification card to the patient 20, as at 140. Alternatively, plan sponsor 25 may distribute the identification card to the patient/subscriber 20.

In operation, the patient 20 will first receive a prescription from a physician or other proper prescriber. The patient 20 then presents their prescription and their prescription benefit card as at 150 to a participating pharmacy 40, either by phone, facsimile or in-person for dispensing. As an example embodiment of the present invention, the process will be described for a patient visiting a pharmacy in person. When presented with a patient's prescription and prescription benefit card as at 150, the participating pharmacy 40 processes that claim by sending it to the claims processor 50 via the electronic means for telecommunication, as at 170. The claims processor 50 begins adjudicating the claim by correlating it to the eligibility file for the subscriber/patient 20. The eligibility of the patient 20 to receive benefits under the Plan 14 is then checked. If at any point during claim processing the claim fails to meet the eligibility file parameters and/or algorithms, the claim is declined and the reason for declination is sent back to the pharmacy as at 210, which may then inform the patient of the reason for the prescription benefit being declined. If the patient 20 is eligible, the claim is further processed in accordance with the parameters of the plan design portion of the eligibility file and any other applicable algorithms. Example algorithms may include, but are not limited to, error checking, cross-referencing and quality-control reviews. After the claims processor 50 processes the claim, a determination is made as to whether or not the prescription should be filled. During this adjudication process, the prescription claims processor 50 may conduct a DRR to check for potential drug-related conflicts such as adverse reactions and interactions.

After the claim has passed eligibility, algorithm and DRR reviews, a charge request inquiry is sent as at 200 to a credit card clearinghouse ("CCCH") 70 by the claims processor 50 to confirm that the credit card information stored in the eligibility file for the patient 20 is still valid and that new charges for the claim will be accepted. If the CCCH 70 determines that the patient credit card is not current or is otherwise invalid, a message is sent as at 206 from the CCCH to the pharmacy 40 via the prescription claims processor 50, as at 210, to advise the patient/subscriber 20 that they are not currently eligible for prescription benefits. The patient 20 is typically further advised to call their plan sponsor 25 for additional assistance.

Once the credit of patient 20 is verified the CCCH 70 instructs the prescription claims processor 50 to proceed with the processing of the claim, as at 206. The CCCH 70 places a charge on the patient's 20 credit card account, as at 202. The credit card account of the patient 20 is charged an amount equal to the cost of the prescription minus the amount of co-payment to be tendered directly to the pharmacy 40 by the patient, as at 215. The CCCH 70 also issues the PBM 30 a payment in the form of a credit for the remaining balance of the cost of the prescription, minus predetermined processing service fees, as at 230. The credit may be issued on a per-transaction basis. Alternatively, a plurality of credits from at least one patient 20 may be aggregated and issued to the PBM periodically.

After receiving approval from the CCCH 70 to proceed at 206, the claims processor 50 sends instructions 210 to the pharmacy 40 to fill the prescription. The claims processor 50 provides the pharmacy 40 with information regarding the amount of co-payment 215 to collect from the patient 20, the total cost for the prescription, and the pharmacy's share of any remaining balance of the prescription transaction. The pharmacy 40 then collects the co-payment 215 from the patient 20 and dispenses the prescription as at 220. The PBM 30 pays the participating pharmacy 40 a predetermined portion of the price of the prescription transaction as at 240, in accordance with the service agreement entered into at 100. The payment may be made on a per-transaction basis, or the payments may be aggregated by the PBM 30 and provided periodically to the pharmacy 40.

Figure 2:
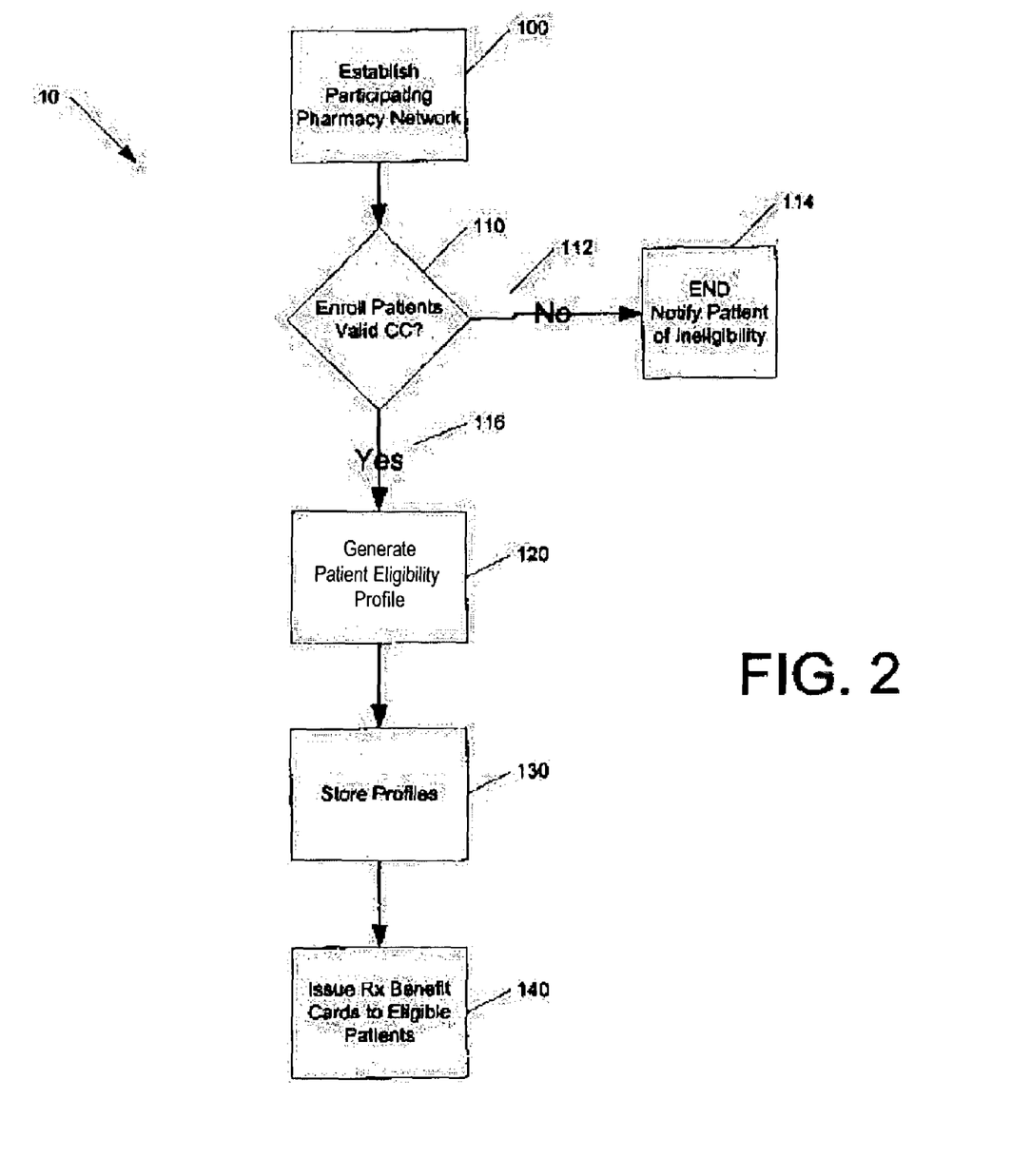
FIG. 2 is a flow chart diagram for establishing a framework for a discount prescription benefit card program in accordance with an embodiment of the present invention.

Referring now to FIG. 2 in combination with FIG. 1, a flow chart diagram is shown which details a method for establishing a framework 10 for a discount prescription benefit card Plan 14, in accordance with an embodiment of the present invention. At step 100 a network of participating pharmacies is established. The pharmacies may be corporately owned, franchised, independently owned, or a combination of ownership types. Further, the pharmacies in the network may be organized in any manner desired to support the operation of the Plan 14. For example, the pharmacies may be grouped geographically, such as in regions. A plurality of conditions and requirements may be established for the pharmacies participating in the network. Example conditions and requirements may include data collection and reporting, pricing, discounting, apportioning of charges, patient counseling and advocacy, product delivery, quality standards, continuing education, and inventory content and levels. At step 110 subscriber/patients 20 are enrolled in the Plan 14. The enrollment step 110 may include screening of potential subscribers 20. Screening criteria may include verification that the candidate is eligible for participation in the Plan 14. For example, a Plan 14 sponsored by an employer typically requires that the subscriber be employed part-time or full-time by the sponsoring employer. In addition, credit card account information for each patient 20 is collected and validated at step 110. Credit card validation activities include verifying that the credit card information is correct, that the credit account is valid, and that the patient's account is current and available to accept new charges. If the potential subscriber 20 does not meet the criteria for participation in the Plan 14 or if the potential subscriber does not have an acceptable credit card account, the subscriber is notified at step 114 of their ineligibility, as at step 112. If the subscriber is eligible for participation at 116, an eligibility profile is assembled at step 120. As previously discussed in detail, the eligibility profile includes patient 20 information, credit card account information, and Plan 14 design information. The plan design information may include details of coverage, limits, and conditions for the Plan 14 as they apply to a particular patient 20. At step 130 eligibility profiles for all subscribers 20 in the Plan 14 are collected and stored for later use in adjudicating claims. At step 140 identification cards for the Plan 14 are issued to subscriber/patients 20. The identification cards may include the patient's name, plan identification information, plan sponsor name and any other data desired to facilitate operation of the Plan 14.

Figure 3:
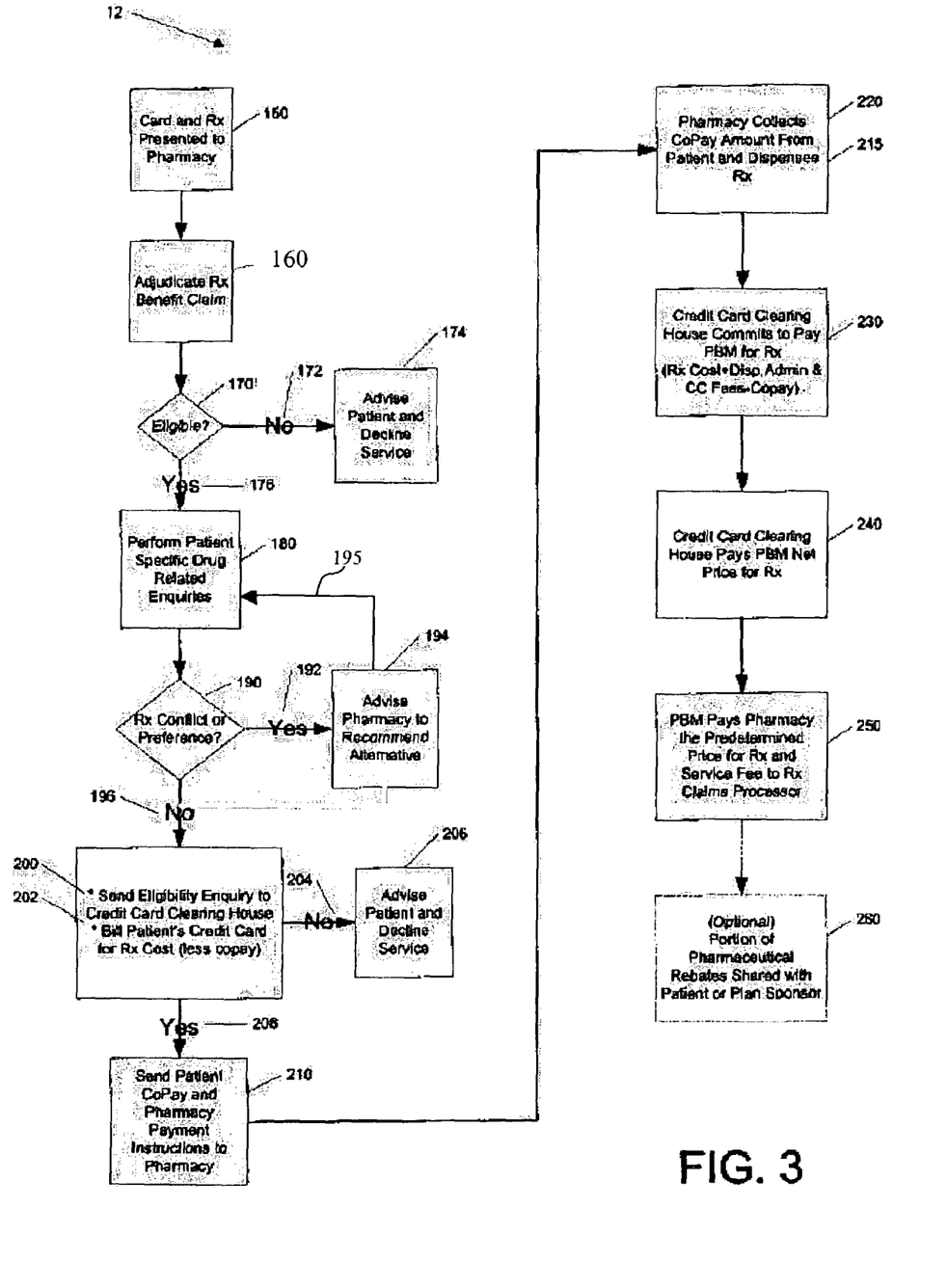
FIG. 3 is a flow chart diagram for processing claims for a discount prescription benefit card program in accordance with the present invention.

Referring to FIG. 3 in combination with FIG. 1, details are shown of the processing 12 of prescriptions and claims for benefits according to an embodiment of the present invention. At step 150 the patient 20 presents a prescription to the pharmacy along with the patient's drug benefits plan identification card. At step 160 the pharmacy adjudicates the patient's 20 claim by first checking to see if the patient is currently eligible to participate in the Plan, as at 170. As previously detailed above and shown in FIG. 1, this step is preferably accomplished by means of an inquiry from the pharmacy to a claims processor 50, which may be remotely located. If the patient 20 is not eligible for benefits, as at 172, the patient is advised at step 174 that the claim is declined. If the patient 20 is found to be eligible, as at 176, the pharmacy and/or claims processor may perform patient-specific drug-related evaluations at 180. The evaluations may include DRR and other drug adverse reaction and/or interaction reviews. In addition, the prescription is reviewed at 180 to see if the drugs prescribed are on-formulary. If a potential adverse reaction or interaction is identified or if a less expensive drug is available, as at 192, a recommendation for alternatives is made to the pharmacy 40 as at 194 and 195. After completing the prescription conflict and preference check at 190, claims processing is advanced at 196 to make payment for the prescription. An eligibility check of the patient's credit card is made at step 200. If the credit card is not in a condition to accept new charges, as at 204, the patient is notified at 206 that the service is declined. If the credit card is valid, the patient's credit card is billed for the prescription charge, less the co-payment defined in the Plan 14, as at 202. At step 208, a communication is sent to the pharmacy providing prescription fulfillment and co-payment instructions, as at 210. The pharmacy then collects the co-payment from the patient 20 at step 220, and dispenses the prescription at 215. At step 230 the CCCH 70 promises to pay the PBM 30 for the net prescription charges, and then makes payment at step 240. The net prescription charge is equal to the cost of the prescription plus any dispensing, administrative and credit card fees, minus the predetermined co-pay. At step 250 the PBM 30 pays the pharmacy 40 a predetermined amount for the prescription transaction. The PBM 30 also pays the claims processor 50 a service fee at step 250. At step 260, the patient 20 may optionally be awarded a rebate for their contribution to market-shifting, as will be discussed in more detail below.

As previously noted, communications between the parties 25, 30, 40, 50, 60, 70 are preferably accomplished via the electronic means for telecommunication. The patient 20 may also optionally be linked to one or more of the parties 25, 30, 40, 50, 60, 70 via the electronic means for telecommunication. Using electronic means for telecommunication, the amount of time required to adjudicate a claim is greatly reduced, and may be accomplished during the patient's 20 visit to the pharmacy 40.

In an alternate embodiment of the present invention, the PBM 30 may enter into agreements with at least one pharmaceutical company 80 whereby the pharmaceutical company provides financial incentives to the PBM in exchange for any gains in market share for its products as a result of the PBM's efforts. The PBM 30 may effect a gain in market share for the products by specifying the products in its formulary (or other preference lists) as preferred over other therapeutically equivalent medications. The PBM 30 monitors prescription claims data to determine usage of the pharmaceutical company's 80 products by the subscribers 20. The PBM 30 periodically provides the pharmaceutical company 80 with this usage data as at 75, preferably using the electronic means for telecommunications. If the PBM 30 contributes to an increase in the market share for a particular pharmaceutical company 80, a financial rebate may be provided to the PBM by the pharmaceutical company, as at 90. In one embodiment of the present invention, the Plan 14 is designed to share at least a portion of the financial rebates received by the PBM 30 with the patient 20, as at 95, when the patient voluntarily switches to a preferred medication or a lower-cost treatment alternative that is effective in moving the market share in favor of particular pharmaceutical products. The patient 20 may optionally receive a greater share of the rebates when their decisions have contributed to a greater extent to making that market share higher for the particular products. In this embodiment of the present invention, the patient would receive a portion of the rebate in proportion to their contribution to the shift in market share that improved the market share for that pharmaceutical product.

As an example of market share rebates, consider a patient who is evaluating a number of medically equivalent products to treat hyper-colesterolemia, such as a hydroxy-methylglutaryl ("HMG"). If the patient is not currently using HMGs, then beginning to do so would contribute neither positively or negatively to the market share. In other words, the new use of the HMG would be an increase in the market rather than a shift in market share. Thus, the patient 20 would not qualify for sharing of any rebate with the PBM 30, since no market share shift has occurred. However, if the patient 20 is currently using an HMG and switches to a brand designated as "preferred" by the PBM 30, the patient's elective contribution to the shift in market share would make the patient eligible for sharing of a rebate provided to the PBM by the pharmaceutical company 80.

In yet another embodiment of the present invention a cost savings benefit is offered to plan sponsors 25 who are "self-funded." Self-funded sponsors may be generally defined as sponsors who underwrite the cost of the prescription benefits plan 14 directly, rather than paying premiums to a third party such as an insurer. Self-funded plans may or may not be 100% co-payment plans. Some self-funded plans are "capped" in that the subscriber 20 is required to pay only the co-payment or other portion of the prescription cost, while the balance of the cost is borne by the sponsor 25. As is well-known, the cost of providing prescription drug benefits is increasing at a greater rate every year. As a result, sponsors 25 are highly motivated to decrease the cost of their pharmacy benefit. The design of the Plan 14 may include such cost-cutting techniques as generic substitution, therapeutic interchange, formularies, rebates, multi-tier co-pays and the sharing of rebates with the subscriber.

A multi-tier co-pay benefit program is configured such that there may be two or more branded drugs and one generic drug listed for each medication in a list of acceptable drugs. The plan then provides for different amounts of co-payments wherein the lowest co-payment would apply to generic products as an encouragement for subscriber/patients 20 to choose these lower cost alternatives. A higher amount of co-payment would apply to brand-name products that are on-formulary. For those pharmaceutical products that are off-formulary, an even higher amount of co-payment would apply. Thus, rather than not covering the off-formulary drug at all under the plan, the third level co-payment provides for the patient to pay a greater predetermined portion. For example, the Plan 14 may have three tiers of co-payments in amounts of $5, $10, and $30, where the $5 co-payment applies to a generic prescription, a $10 co-payment is charged for an on-formulary brand-name prescription, and a $30 co-payment is charged if the patient elects a medication that is not on-formulary.

Subscriber/patients 20 in a self-funded, capped plan may tend to use a higher quantity of more expensive products than is medically necessary, due in part to efforts by the pharmaceutical companies 80 to circumvent the various cost-saving techniques employed by PBMs 30. These efforts include appealing directly to the patient 20 via direct-to-consumer advertising, omnipresent in magazines, newspapers, radio and television. The pharmaceutical companies 80 are actively promoting better health and improved medical treatment outcomes through use of their new, generally more expensive products. Consequently, there is pressure on the patients 20 and their doctors to increase the use of the new products. These newer products are typically off-formulary. However, even for drugs that are on-formulary, this directed consumer advertising has motivated many patients 20 to ask their physicians for more expensive products than the physician would normally prescribe for the patient to achieve the same outcome. In some cases a patient 20 may ask their physician for prescription medication to treat a minor or perceived problem that the patient was unaware of prior to exposure to the advertising. Under the typical self-funded, capped prescription benefit plan which may have only one or two co-payment levels, the patient has little financial incentive to reduce their prescription costs. Further, an employee participating in a self-funded, capped prescription benefit plan may perceive a higher-priced prescription as a greater employee benefit.

To counter this cost-inefficient practice, in one embodiment of the present invention that may be especially relevant in a self-funded plan, a prescription benefits plan utilizes the subscriber's 20 credit card in the prescription transaction much in the same fashion as under the 100% co-payment Plan 14. In this embodiment, the patient 20 pays a percentage of the prescription price to the pharmacy 40 at the time of dispensing with the balance of the price being charged to their credit card by the PBM 30. The self-funded sponsor 25 would then periodically reimburse the patient a portion of their prescription expenditures in an amount that would reward the patient for utilizing generic and on-formulary drugs. This embodiment of the present invention could also include provisions for a multi-tiered co-payment as previously disclosed. In this regard the patient 20 would gain a greater awareness of the cost of the drug products and the effect of their elections on the overall cost to the self-funded sponsor 25. The sponsor 25 may adjust the reimbursement schedule based on the patient's 20 drug specification behavior and whether or not the patient chooses products that are therapeutically equivalent but available at a lower cost. Thus, the self-insured sponsor 25 may pay a greater portion of the cost of the patient's 20 prescription costs if the patient specifies less expensive, therapeutically equivalent medications. The end result is a plan that is beneficial for both the patient and the self-funded sponsor in that both will realize a decreased out-of-pocket cost in their prescription benefit.

The features of the present invention have been described in detail with respect to specific embodiments thereof, but it will be apparent that numerous variations and modifications are possible without departing from the spirit and scope of the inventive embodiments as defined by the claims. Likewise, one skilled in the art will recognize that the order of certain steps in the claims may be combined, deleted or rearranged without departing from the spirit and scope of the inventive embodiments.

What is claimed is:

1. A method of providing prescription benefits to subscribers under a subscriber co-pay plan via an electronic communications network to ensure that the subscriber receives a discounted prescription price, the method comprising the steps of:
   a) identifying a sponsor for a prescription benefits plan;
   b) designing the prescription benefits plan to include a formulary of preferred medications, and to define prescription medications that are covered by the prescription benefits plan;
   c) identifying at least one pharmacy that:
      i) participates in the prescription benefits plan,
      ii) receives prescriptions for medication and prescription benefit claims from subscribers, and
      iii) fulfills the prescriptions for a discounted prescription price;
   d) identifying at least one eligible subscriber having a valid credit or debit account with a creditor or institution and wishing to participate in the prescription benefits plan;
   e) enrolling each eligible subscriber who wishes to participate in the prescription benefits plan and generating an electronic file for each of the eligible subscribers;

f) generating an eligibility profile for each subscriber and storing said eligibility profile in an electronic memory;

g) establishing a prescription benefits manager to administer the prescription benefits plan;

h) establishing a prescription claims processor that:
   i) receives claims over the electronic communications network for prescription benefits from a participating pharmacy;
   ii) adjudicates the claims in accordance with the subscriber's eligibility profile; and
   iii) upon approval of a claim, charges the subscriber's credit or debit account for accepted claims via the electronic communications network, the amount of the charge being equal to the discounted price of the prescription minus a predetermined co-payment which is tendered by the subscriber to the pharmacy at the time of fulfilling the prescription;

i) making a first payment via the electronic communications network by the creditor to the prescription benefits manager, the first payment being equal to the amount charged to the subscriber's account minus a first predetermined service fee to be retained by the creditor;

j) making a second payment via the electronic communications network by the prescription benefits manager to the pharmacy, the second payment being equal to a predetermined portion of the discounted prescription price; and k) making a third payment via the electronic communication network by the prescription benefits manager to the claims processor, the third payment being equal to a second predetermined service fee, wherein the second payment and the third payment are funded by the first payment and whereby the sum of the pre-determined co-payment and the amount charged to the subscriber's account is the discounted prescription price paid by the subscriber.

2. The method of claim 1 wherein the claims processor further:
   a) performs a drug regimen review prior to approval of a claim; and
   b) advises the pharmacy of the review results.

3. The method of claim 1, further comprising the steps of:
   a) imprinting subscriber information onto identification cards; and
   b) distributing the identification cards to the subscribers.

4. The method of claim 1 wherein the amount of the co-payment is determined by the medication's inclusion, exclusion or ranking in the formulary.

5. The method of claim 1, wherein the adjudication of claims by the claims processor further comprises the steps of:
   a) checking the prescription against the formulary; and
   b) recommending medications to the pharmacy for fulfilling the prescription, the recommendation being determined by formulary preferences.

6. The method of claim 1 wherein the prescription benefits manager further generates reports relating to subscriber prescription claims.

7. The method of claim 1 wherein the prescription benefits manager further:
   a) identifies at least one market for at least one selected prescription medication, for at least one pharmaceutical company;
   b) accumulates usage data regarding consumption of the at least one selected prescription medication by the subscribers;
   c) periodically provides the usage data to the pharmaceutical company; and
   d) receives an incentive from the pharmaceutical company as a result of an increase in market share for the selected prescription medication among the subscribers.

8. The method of claim 7, further comprising the step of sharing at least a portion of the incentive with subscribers who contribute to the increase in market share.

9. The method of claim 8 wherein the amount of the incentive shared with a subscriber is related to that subscriber's contribution to the increase in market share.

10. The method of claim 1 wherein an electronic means for telecommunication is used to link at least two of the participants comprising the subscriber, the prescription benefits plan sponsor, the pharmacy, the prescription benefits manager, the claims processor and the creditor or institution.

11. The method of claim 7 wherein the electronic communications network is used to link the pharmaceutical company and the prescription benefits manager.

12. The method of claim 1 wherein the first payment is in the form of a credit to an account which is periodically paid out to the prescription benefits manager.

13. The method of claim 1 wherein the sponsor reimburses the subscriber in an amount related to the subscriber's participation in formulary-determined preferences.

* * * * *

UNITED STATES PATENT AND TRADEMARK OFFICE
CERTIFICATE OF CORRECTION

PATENT NO. : 7,657,437 B2 Page 1 of 1
APPLICATION NO. : 10/608265
DATED : February 2, 2010
INVENTOR(S) : Ralph F. Kalies It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1177 days.

Signed and Sealed this

Thirtieth Day of November, 2010

David J. Kappos
*Director of the United States Patent and Trademark Office*